US010369559B2

(12) United States Patent
Qin et al.

(10) Patent No.: US 10,369,559 B2
(45) Date of Patent: Aug. 6, 2019

(54) COMPOSITE CATALYST, PREPARATION PROCESS THEREOF, AND PROCESS FOR CATALYZING THE TRIMERIZATION OF BUTADIENE USING THE COMPOSITE CATALYST

(71) Applicants: WANHUA CHEMICAL GROUP CO., LTD., Yantai (CN); WANHUA CHEMICAL (NINGBO) CO., LTD., Yantai (CN)

(72) Inventors: Lei Qin, Yantai (CN); Weiqi Hua, Yantai (CN); Ruihua Cheng, Yantai (CN); Yuan Li, Yantai (CN); Baiping Liu, Yantai (CN); Bingbo Hu, Yantai (CN)

(73) Assignees: Wanhua Chemical Group Co., Ltd., Shandong (CN); Wanhua Chemical (Ningbo) Co., Ltd., Shandong (CN)

( * ) Notice: Subject to any disclaimer, the term of this patent is extended or adjusted under 35 U.S.C. 154(b) by 343 days.

(21) Appl. No.: 14/422,639

(22) PCT Filed: May 9, 2013

(86) PCT No.: PCT/CN2013/075393
§ 371 (c)(1),
(2) Date: Feb. 19, 2015

(87) PCT Pub. No.: WO2014/032439
PCT Pub. Date: Mar. 6, 2014

(65) Prior Publication Data
US 2015/0231623 A1      Aug. 20, 2015

(30) Foreign Application Priority Data

Sep. 1, 2012  (CN) .......................... 2012 1 0325296

(51) Int. Cl.
| | | |
|---|---|---|
| *B01J 31/38* | (2006.01) | |
| *C07C 2/46* | (2006.01) | |
| *B01J 31/02* | (2006.01) | |
| *B01J 31/12* | (2006.01) | |
| *B01J 31/14* | (2006.01) | |
| *B01J 37/04* | (2006.01) | |
| *B01J 37/08* | (2006.01) | |
| *B01J 31/22* | (2006.01) | |

(52) U.S. Cl.
CPC ........... *B01J 31/38* (2013.01); *B01J 31/0209* (2013.01); *B01J 31/0212* (2013.01); *B01J 31/0215* (2013.01); *B01J 31/0229* (2013.01); *B01J 31/0232* (2013.01); *B01J 31/122* (2013.01); *B01J 31/143* (2013.01); *B01J 31/146* (2013.01); *B01J 37/04* (2013.01); *B01J 37/08* (2013.01); *C07C 2/465* (2013.01); *B01J 31/128* (2013.01); *B01J 31/2226* (2013.01); *B01J 2231/20* (2013.01); *C07C 2531/02* (2013.01); *C07C 2531/14* (2013.01); *C07C 2531/38* (2013.01)

(58) Field of Classification Search
None
See application file for complete search history.

(56) References Cited

U.S. PATENT DOCUMENTS

| | | | |
|---|---|---|---|
| 3,523,980 A | 8/1970 | Sullivan | |
| 3,634,528 A | 1/1972 | Itakura | |
| 3,636,174 A | 1/1972 | Nakamura | |
| 3,655,795 A | 4/1972 | Sullivan | |
| 3,658,926 A | 4/1972 | Morikawa | |
| 3,878,258 A | 4/1975 | Rapoport | |
| 4,487,844 A * | 12/1984 | Parlman | C08F 10/00 502/104 |
| 5,064,795 A * | 11/1991 | McDaniel | C08F 10/00 502/104 |
| 6,559,249 B2 * | 5/2003 | Yang | C08F 110/02 502/103 |

FOREIGN PATENT DOCUMENTS

| | | |
|---|---|---|
| CN | 1555349 A | 12/2004 |
| CN | 102872916 A | 1/2013 |
| EP | 1685898 A1 | 8/2006 |
| WO | 2011139034 A2 | 8/2006 |

OTHER PUBLICATIONS

Xinyuan Shen, Chemical Fiber Manuel, China Textile & Apparel Press, Sep. 1, 2008.
International Search Report for corresponding application PCT/CN2013/075393 filed May 9, 2013; dated Aug. 22, 2013.

* cited by examiner

*Primary Examiner* — Yun Qian

(57) ABSTRACT

The present invention relates to a composite catalyst, preparation process thereof, and process for catalyzing the trimerization of butadiene using the composite catalyst. The composite catalyst comprises: (A) a titanium compound catalyst active component, (B) an organometallic compound co-catalyst component, (C) a sulfoxide compound catalyst-modifying component, (D) a monoester compound catalyst-modifying component, and (E) a solvent component. The composite catalyst has advantages of excellent selectivity, high catalytic activity, easy preparation and so on.

9 Claims, No Drawings

COMPOSITE CATALYST, PREPARATION PROCESS THEREOF, AND PROCESS FOR CATALYZING THE TRIMERIZATION OF BUTADIENE USING THE COMPOSITE CATALYST

FIELD OF THE INVENTION

The present invention relates to a composite catalyst, preparation process thereof, and process for catalyzing the trimerization of butadiene using the composite catalyst. The composite catalyst has advantages of excellent selectivity, high catalytic activity, easy preparation and so on.

BACKGROUND OF THE INVENTION

Butadiene is one of the three important olefins produced in petrochemical process, and has a wide range of application perspective. At present, butadiene is primarily used as the raw material for producing high molecular synthetic material such as polybutadiene rubber, styrene butadiene rubber (SBR) and so on in bulk. But with the development of science and technology, butadiene oligomer products production technology becomes more mature, its application becomes more extensive, and the researchers become more interested in studying oligomerization technology. Among them, an attracting one is the trimerization of butadiene to 1,5,9-cyclododecatriene (CDT). CDT is an important fine chemical intermediate, and its very important uses are the production of engineering plastics nylon 12, polyamide, flame retardant, and certain macrocyclic musks. In order to obtain nylon 12, CDT is firstly converted to polyol, and then formed into nylon 12. Polyamides (PA) obtained by polycondesation of diamines and diacids or by polymerization of lactams are the most popular and commonly used polymers. Among the polyamides, only poly-$\epsilon$-caprolactam (PA6), poly-$\omega$-undecalactam (PA11) and poly-$\omega$-dodecalactam (PA12) can be available for industrial use. PA12 contains less residual monomers in the molecule, has a low atmospheric moisture absorption capacity, and can maintain good toughness at very low temperatures (−70° C.). Thus, PA12 is often used to manufacture high quality plastic articles, particularly those intended to use in the environment varied frequently in humidity or those required to have good mechanical properties, heat insulation and electrical insulation properties. In addition, it can be used in the protective sheath of cables, ducts and pipes, pneumatic brake pipes and pipelines of the fuel system for automobiles. Most of the known methods for producing PA12 use cyclododecatriene prepared by trimerization of butadiene as the raw material.

Since Wilke separated a metal nickel coordination complex from butadiene oligomers, the cyclooligomerization process of butadiene has been set forth. And the theory of the butadiene cyclooligomerization and the production technology have gradually come to maturity. CDT was used as the dodecalactam raw materials of nylon 12 from 1970s in the former West Germany etc., and therefore there have been cases of the development of industrial scale production. A bromination reaction product of CDT, i.e., hexabromocyclododecane (HBCD), has been used as the flame retardant of engineering plastics which will be one of the needs for CDT in future. In China, the use of HBCD as the flame retardant for textile was studied in lab, but was not practiced in the industrial application. The macrocyclic muscone (TM-II) products with natural perfumes from animal have been prepared by Japan Toray Industries, Inc. using CDT as the raw material and sold in the market. With the enlarged application of the CDT products, there is an increasing demand for CDT in the market.

Homogeneous titanium-based Ziegler-Natta catalysts have been applied for the industrial trimerization of butadiene since 1956, and still have the disadvantages of low selectivity, poor activity, etc. These catalyst systems have been studied in Dalian Institute of Chemical Physics, Chinese Academy of Sciences and the Research Institue of Rubber Factory of SINOPEC BEIJING YANSHAN COMPANY at the lab- and pilot-scale in 1990s, but the industrial application is not reported.

U.S. Pat. No. 3,634,528 disclosed the trimerization of butadiene using organotitanium/hydrocarbyl aluminium chloride as the catalyst and benzene as the solvent, having the conversion of butadiene of at most 95.6%, but there is no data about the catalyst activity and CDT selectivity of the reaction products. U.S. Pat. No. 3,523,980 disclosed the trimerization of butadiene using sesquiethyl aluminum chloride/oxygen/titanium (IV) compound as the catalyst system. The disclosure discussed the influences of the molar ratio of sesquiethyl aluminum chloride/titanium (IV) compound to oxygen on the reactivity, but the selectivity was not described. U.S. Pat. No. 3,658,926 disclosed the trimerization of butadiene using tetrabutyl titanium/triphenyl phosphine/triethyl aluminium as the catalyst system, but the activity and selectivity were not described. U.S. Pat. No. 3,655,795 disclosed the trimerization of butadiene using a titanium compound/an organoaluminium compound/a promoter as the catalyst, and mainly discussed the influences of different promoters, such as water, oxgenated compounds, oxygen or oxygen containing gases or liquids on the catalytic properties. U.S. Pat. No. 3,636,174 also disclosed a similar catalyst, which was different from that of U.S. Pat. No. 3,655,795 only in the promoter. Using the sulfoxide as the promoter, its catalytic activity may be up to 11238.8 g CDT/g $_{Ti}$/h, but the CDT selectivity of the reaction products was not described. The Research Institue of Rubber Factory of SINOPEC BEIJING YANSHAN COMPANY also studied the catalyst system in 1990s, and found that the catalyst has the optimal catalytic activity of 18220 g CDT/g $_{Ti}$/h, and CDT selectivity of the reaction products of 93.84% at high pressure. Its catalytic activity and CDT selectivity are still low.

Although the process for catalyzing the trimerization of butadiene to CDT using the titanium-based catalysts has been applied for the industrial production since 1956, it still has suffered the low catalyst activity, low selectivity etc.

SUMMARY OF THE INVENTION

The present invention provides a composite catalyst, preparation process thereof, and process for catalyzing the trimerization of butadiene using the composite catalyst. With this simple- and cheap-prepared composite catalyst, the reaction for preparation of 1,5,9-cyclododecatriene (CDT) by catalyzing the trimerization of butadiene provides high catalytic activity, excellent CDT selectivity and so on.

The present invention is described as below.

The composite catalyst of the present invention comprises (A) a titanium compound catalyst active component, (B) an organometallic compound co-catalyst component, (C) a sulfoxide compound catalyst-modifying component, (D) a monoester compound catalyst-modifying component, and (E) a solvent component.

The titanium compound catalyst active component (A) of the composite catalyst comprises one or more selected from the group consisting of titanium (II) compounds, titanium (III) compounds and titanium (IV) compounds. The titanium (II) compounds comprise $TiCl_2$, $TiCl_xR_{2-x}$ or $TiCl_x(OR)_{2-x}$; the titanium (III) compounds comprise $TiCl_3$, $TiCl_YR_{3-Y}$ or $TiCl_Y(OR)_{3-Y}$; the titanium (IV) compounds comprise $TiCl_4$, $TiCl_zR_{4-z}$ or $TiCl_z(OR)_{4-z}$, wherein X=1, Y=1 or 2, Z=1, 2 or 3, OR is alkoxy, R is alkyl having 1~20 carbons, including but not limited to methyl, ethyl, propyl, n-butyl, iso-butyl, pentyl, hexyl.

The titanium compound catalyst active component (A) of the composite catalyst is preferably selected from one or more of titanium dichloride, di-n-butyl titanium, titanium ethyl chloride, titanium trichloride, titanium triethoxide, titanium tetrachloride, titanium tetraethoxide, and triethoxytitanium chloride.

The organometallic compound co-catalyst component (B) of the composite catalyst comprises one or more selected from the group consisting of organo-lithium compounds, organoboron compounds and organoaluminum compounds. The organo-lithium compounds comprise one or more alkyl lithium compounds of the formula $LiR^1$; the organoboron compounds comprise one or more selected from the group consisting of trialkyl boron of the formula $BR^1_3$, dialkyl alkoxy boron of the formula $BR^1_2OR^1$, dialkyl boron halide of the formula $BR^1_2X$; the organoaluminum compounds comprise one or more selected from the group consisting of trialkyl aluminium of the formula $AlR^1_3$, dialkyl alkoxy aluminium of the formula $AlR^1_2OR^1$, dialkyl aluminium halide of the formula $AlR^1_2X$, alkyl aluminium dihalide of the formula $AlR^1X_2$, sesquialkyl aluminum chloride of the formula $Al_2R^1_3X_3$, and aluminoxane, wherein $R^1$ is the alkyl having 1~12 carbon atoms, including but not limited to methyl, ethyl, n-propyl, isopropyl, n-butyl, isobutyl, n-pentyl, n-hexyl, n-heptyl, n-octyl, n-nonyl, n-dodecyl; X is halogen comprising fluorine, chlorine, bromine or iodine, preferably chlorine. Said aluminoxane is the reaction product of alkyl aluminium and water.

The organometallic compound co-catalyst component (B) of the composite catalyst is preferably selected from one or more of methyl lithium, n-butyl lithium, n-hexyl lithium, sec-butyl lithium, trimethyl boron, triethyl boron, triethyl aluminium, triisobutyl aluminium, diethyl ethoxy aluminium, aluminium diethyl monochloride, aluminium ethyl dichloride, sesquiethyl aluminum chloride, and methyl aluminoxane.

The sulfoxide compound catalyst-modifying component (C) of the composite catalyst comprises one or more selected from the group consisting of the compounds of formula $(R^2R^3)S=O$ (wherein $R^2$ is halogen, or optionally substituted or unsubstituted alkyl or aryl having 3~20 carbons, $R^3$ is halogen, or optionally substituted or unsubstituted alkyl or aryl having 3~20 carbons, and $R^2$ and $R^3$ may be identical or different) and trimethylsulfoxonium iodide.

The sulfoxide compound catalyst-modifying component (C) of the composite catalyst is preferably selected from one or more of dimethyl sulfoxide, thionyl chloride, diphenyl sulfoxide, and trimethylsulfoxonium iodide.

The monoester compound catalyst-modifying component (D) of the composite catalyst comprises one or more selected from the group consisting of the monoester compounds of formula $R^4COOR^5$, wherein $R^4$ is a substituted or unsubstituted alkyl or aryl having 3~20 carbons, $R^5$ is substituted or unsubstituted alkyl or aryl having 3~20 carbons, and $R^4$ and $R^5$ may be identical or different. If substituted, the substituent(s) includes but not limited to halogen, hydroxyl, carboxyl, amino, sulfo group.

The monoester compound catalyst-modifying component (D) of the composite catalyst is preferably selected from one or more of methyl methacrylate, ethyl mechacrylate, butyl methacrylate, methyl formate, ethyl formate, butyl formate, methyl acetate, ethyl acetate, butyl acetate, methyl p-hydroxybenzoate, ethyl p-hydroxybenzoate, butyl p-hydroxybenzoate, methyl aminobenzoate, ethyl aminobenzoate, butyl aminobenzoate, methyl p-benzenesulfonate, ethyl p-benzenesulfonate, butyl p-benzenesulfonate, methyl benzoate, ethyl benzoate, butyl benzoate, methyl salicylate, ethyl salicylate and butyl salicylate.

The solvent component (E) of the composite catalyst can be any one of the solvents which may be used for the oligomerization or polymerization of olefins or diolefins, and comprises one or more selected from the group consisting of alkanes and arenes (or aromatic hydrocarbons) having 3~20 carbons, and 1,5,9-cyclododecatriene.

The solvent component (E) of the composite catalyst is preferably selected from one or more of propane, n-butane, isobutane, n-pentane, isopentane, neopentane, n-hexane, cyclohexane, n-heptane, n-octane, benzene, toluene, xylene, or CDT.

The contents of the components in the composite catalyst are shown as below:

The molar ratio of the organometallic compound co-catalyst component (B) to the titanium compound catalyst active component (A) is 1~1000:1, preferably 20~500:1.

The molar ratio of the sulfoxide compound catalyst-modifying component (C) to the titanium compound catalyst active component (A) is 0~50:1, preferably 1~30:1.

The molar ratio of the monoester compound catalyst-modifying component (D) to the titanium compound catalyst active component (A) is 0.1~50:1, preferably 1~30:1.

The molar ratio of the solvent component (E) to the titanium compound catalyst active component (A) is 0~50000:1, preferably 5000~30000:1.

The process for preparing the above described composite catalyst comprises:

adjusting the temperature of the oxygen-free and water-free reaction system for preparing the composite catalyst to the preparation temperature of the composite catalyst, and to the reaction system adding the titanium compound catalyst active component (A), the organometallic compound co-catalyst component (B), the sulfoxide compound catalyst-modifying component (C), the monoester compound catalyst-modifying component (D), and the solvent component (E) in a specified proportion under stirring, wherein the time needed for preparing the composite catalyst is 15~600 min, preferably 20~300 min, timing from the end of addition of all the components, the temperature of preparing the composite catalyst is 20~120° C., preferably 25~80° C. During the preparation, nitrogen or helium or argon, preferably nitrogen, is introduced continuously.

In the above-described process for preparing the composite catalyst, the titanium compound catalyst active component (A), the organometallic compound co-catalyst component (B), the sulfoxide compound catalyst-modifying component (C), the monoester compound catalyst-modifying component (D), and the solvent component (E) may be added in any order. The organometallic compound co-catalyst component (B), the monoester compound catalyst-modifying component (D), and the solvent component (E) are added in each batch in any order, respectively.

The process for preparing 1,5,9-cyclododecatriene by catalyzing the trimerization of butadiene with the composite catalyst of the present invention comprises the following steps:

adding the composite catalyst and a solvent for trimerization to the trimerization reaction system, wherein the molar ratio of the solvent for trimerization to the titanium compound catalyst active component (A) is 10000~50000:1, preferably 18000~30000:1;

introducing the butadiene continuously to start the reaction, wherein the temperature for the trimerization is 20~200° C., preferably 25~120° C.; the pressure for the trimerization is 0.1~1 MPa, preferably 0.2~0.7 MPa; and the time for the trimerization is 10~600 min, preferably 15~300 min;

adding the termination agent to terminate the reaction, wherein the molar ratio of the termination agent to the titanium compound catalyst active component (A) of the composite catalyst is 0~10:1, preferably 0.1~5:1.

The solvent for trimerization can be any one of the solvents which may be used for the oligomerization or polymerization of olefins or diolefins, and comprises one or more selected from the group consisting of alkanes and arenes having 3~20 carbons, and 1,5,9-cyclododecatriene, preferably propane, n-butane, isobutane, n-pentane, isopentane, neopentane, n-hexane, cyclohexane, n-heptane, n-octane, benzene, toluene, xylene, or CDT.

The termination agent described in the present invention may be one or more selected from the group consisting of the compounds which are known in the field of olefin polymerization to be chemically reacted with the titanium compound catalyst active component (A) and deactivate the latter, and comprises water, monohydroxy alcohol, or the mixture of water and monohydroxy alcohol in any proportion, wherein the monohydroxy alcohol is preferably methanol, ethanol or n-butanol.

The catalysis mechanism of the present composite catalyst is described as below:

after the titanium compound is reduced by the organometallic compound co-catalyst, there will be vacancies in the electron cloud around the titanium atom, the titanium atom is firstly complexed with a butadiene molecule, and then complexed with two other butadiene molecules in order, at the same time, under the traction effect of the titanium electron cloud, the three butadiene molecules each break one double bond and are linked to each other, and finally the titanium compound is eliminated under the action of one butadiene molecule and the organometallic compound, and the three butadiene molecules are formed to one CDT molecule;

one butadiene molecule is further complexed around the position of the eliminated titanium, and the above steps will be repeated again and again, thereby CDTs continue to be formed.

The primary effect of adding the monoester compound catalyst-modifying component is to increase the electron cloud density of titanium, promote the complexing capacity of butadiene with titanium, and by virtue of the steric effect, can control the polymerization rate of the trimerization product, so as to improve catalytic activity and CDT selectivity.

the present invention has the following advantages compared to the prior art:

(1) The present invention provides a composite catalyst and preparation process thereof. The preparation of the composite catalyst is simple, and can be used for catalyzing the trimerization of butadiene to CDT;

(2) The composite catalyst of the present invention shows a higher activity than any existing catalysts in catalyzing the trimerization of butadiene, which may be up to 20000 g CDT/g $_{Ti}$/h or more.

(3) The composite catalyst of the present invention shows a higher CDT selectivity than any existing catalysts, which may be up to 95% or more.

THE MODE OF CARRYING OUT THE INVENTION

The present invention will be described in greater detail in conjunction with the following specific examples, but the present invention should not be interpreted to be limited to these examples.

The following instruments and measuring conditions are used in the present invention. The amount of CDT contained in a reaction liquid is measured by gas chromatography internal standard method using GC-2060 gas chromatograph (manufactured by Shanghai Ruimin Instrument Co., Ltd.). The testing conditions of the gas chromatography are as follows: the type of chromatographic column: SE-54, 30 ml×0.25 ml×0.25 ml; the detector used: hydrogen flame detector. The temperature settings of the gas chromatograph: the detector temperature is 250° C., the sample chamber temperature is 200° C., the temperature programmed steps of the column temperature is set to maintain at 50° C. for 3 min, rise to 250° C. at the rate of 25° C./min, and then maintain at 250° C. for 5 min. The gas feeding conditions are as follows: air 250 cm$^3$/min, hydrogen gas 35 cm$^3$/min, carrier gas (nitrogen) 0.7 cm$^3$/min.

The reaction products of the present invention are detected by the gas chromatography internal standard method. The detection method comprises the preparation of a standard curve and the detection of the reaction products.

The preparation of the standard curve: n-dodecane is used as the internal standard of detecting the amount of CDT. Firstly, the standard solutions having CDT/dodecane mass ratio of 0.1, 0.3, 0.5, 0.7, 0.9, 1.1, 1.3, 1.5 are prepared, respectively, and the standard solutions are introduced respectively into the chromatographic column according to the above-said chromatographic conditions to obtain the chromatograms. Secondly, the peak area ratio of CDT and dodecane is calculated according to the chromatograms obtained in the first step, and a standard curve is plotted with area ratio as abscissa and mass ratio as ordinate.

The detection of the reaction products: after the reaction is completed, a small amount of the reaction liquid is weighed, in which a specified amount of dodecane is added and mixed well, and then the resulting mixture is introduced into the chromatographic column, in order to obtain the chromatograms. After calculating the area ratio according to chromatograms, the mass ratio is determined from the above-described standard curve, and the mass of CDT contained in the small amount of weighed reaction liquid is obtained. Further, total mass of CDT contained in all the reaction liquid is obtained, and from this the activity of the catalyst and CDT selectivity of the reaction product are calculated.

Example 1

The preparation of composite catalyst 1: A 500 ml water-free and oxygen-free flask with four necks is immersed in a thermostatic oil bath at the temperature of 50° C. 5.27×10$^{-2}$ mmol of TiCl$_2$(OEt)$_2$, 5.27 mmol of triethyl aluminium, 110 ml of toluene, 1.32 mmol of dimethyl sulfoxide, and 1.32 mmol of methyl benzoate are added into the flask in order, nitrogen gas is introduced into the flask continuously, and the reaction is conducted at 50° C. for 20 min. The composite catalyst 1 is obtained.

The trimerization process: After 78 ml of n-heptane is added to the flask, butadiene is introduced such that the pressure in the flask is maintained at 0.1 MPa, the temperature is raised to 70° C., and the reaction is conducted for 60 min. After that, $5.27 \times 10^{-2}$ mmol of water is added to terminate the reaction. The reaction liquid is weighed and then filtered, and the resulting filtrate is determined by gas chromatography.

As a result, the composite catalyst 1 has the activity of 20423.7 g CDT/g $_{Ti}$/h and CDT selectivity of 95.27%.

Example 2

The preparation of composite catalyst 2: A 500 ml water-free and oxygen-free flask with four necks is immersed in a thermostatic oil bath at the temperature of 70° C. 55 ml of toluene, $5.27 \times 10^{-2}$ mmol of TiCl(OEt)$_3$, 2.64 mmol of triethyl aluminium, 0.264 mmol of trimethylsulfoxonium iodide, and $5.27 \times 10^{-2}$ mmol of methyl formate are added into the flask in order, nitrogen gas is introduced into the flask continuously, and the reaction is conducted at 70° C. for 20 min. The composite catalyst 2 is obtained.

The trimerization process: After 78 ml of n-heptane is added to the flask, butadiene is introduced such that the pressure in the flask is maintained at 0.1 MPa, and the reaction is conducted at the temperature of 70° C. for 120 min. After that, $5.27 \times 10^{-2}$ mmol of ethanol is added to terminate the reaction. The reaction liquid is weighed and then filtered, and the resulting filtrate is determined by gas chromatography.

As a result, the composite catalyst 2 has the activity of 20323.5 g CDT/g $_{Ti}$/h and CDT selectivity of 95.48%.

Example 3

The preparation of composite catalyst 3: The preparation of the composite catalyst 2 in example 2 is repeated using Ti(OEt)$_3$ in place of TiCl(OEt)$_3$.

The trimerization process: According to the trimerization process of example 2.

As a result, the composite catalyst 3 has the activity of 20497.9 g CDT/g $_{Ti}$/h and CDT selectivity of 96.25%.

Example 4

The preparation of composite catalyst 4: A 500 ml water-free and oxygen-free flask with four necks is immersed in a thermostatic oil bath at the temperature of 20° C. 165 ml of toluene, $5.27 \times 10^{-2}$ mmol of TiCl$_4$, 1.32 mmol of dimethyl sulfoxide, 52.7 mmol of n-butyl lithium, and 2.63 mmol of butyl salicylate are added into the flask in order, nitrogen gas is introduced into the flask continuously, and the reaction is conducted at 20° C. for 300 min. The composite catalyst 4 is obtained.

The trimerization process: After 165 ml of toluene is added to the flask, butadiene is introduced such that the pressure in the flask is maintained at 1 MPa, the temperature is raised to 80° C., and the reaction is conducted for 15 min After that, $5.27 \times 10^{-2}$ mmol of water is added to terminate the reaction. The reaction liquid is weighed and then filtered, and the resulting filtrate is determined by gas chromatography.

As a result, the composite catalyst 4 has the activity of 24347.4 g CDT/g $_{Ti}$/h and CDT selectivity of 96.34%.

Example 5

The preparation of composite catalyst 5: A 500 ml water-free and oxygen-free flask with four necks is immersed in a thermostatic oil bath at the temperature of 120° C. 1.05 mmol of sesquiethyl aluminum chloride, 380 ml of n-heptane, $5.27 \times 10^{-2}$ mmol of TiCl$_4$, 1.32 mmol of the mixture (molar ratio 1:1) of thionyl chloride and dimethyl sulfoxide, and 1.32 mmol of ethyl p-hydroxybenzoate are added into the flask in order, nitrogen gas is introduced into the flask continuously, and the reaction is conducted at 120° C. for 600 min. The composite catalyst 5 is obtained.

The trimerization process: Butadiene is introduced to the flask such that the pressure in the flask is maintained at 0.5 MPa, the temperature is raised to 180° C., and the reaction is conducted for 600 min. After that, $5.27 \times 10^{-2}$ mmol of water is added to terminate the reaction. The reaction liquid is weighed and then filtered, and the resulting filtrate is determined by gas chromatography.

As a result, the composite catalyst 5 has the activity of 20324.4 g CDT/g $_{Ti}$/h and CDT selectivity of 98.01%.

Example 6

The preparation of composite catalyst 6: A 500 ml water-free and oxygen-free flask with four necks is immersed in a thermostatic oil bath at the temperature of 70° C. 1.05 mmol of sesquiethyl aluminum chloride, $5.27 \times 10^{-2}$ mmol of TiCl$_4$, 28 ml of toluene, $5.27 \times 10^{-2}$ mmol of dimethyl sulfoxide, and $2.64 \times 10^{-2}$ mmol of ethyl benzoate are added into the flask in order, nitrogen gas is introduced into the flask continuously, and the reaction is conducted at 70° C. for 300 min. The composite catalyst 6 is obtained.

The trimerization process: After 275 ml of toluene is added to the flask, butadiene is introduced such that the pressure in the flask is maintained at 0.1 MPa, the temperature is raised to 100° C., and the reaction is conducted for 300 min. After that, 0.263 mmol of n-butanol is added to terminate the reaction. The reaction liquid is weighed and then filtered, and the resulting filtrate is determined by gas chromatography.

As a result, the composite catalyst 6 has the activity of 20342.1 g CDT/g $_{Ti}$/h and CDT selectivity of 97.83%.

Example 7

The preparation of composite catalyst 7: The preparation of the composite catalyst 6 in example 6 is repeated using ethyl acetate in place of ethyl benzoate.

The trimerization process: According to the trimerization process of example 6.

As a result, the composite catalyst 7 has the activity of 20124.4 g CDT/g $_{Ti}$/h and CDT selectivity of 96.17%.

Example 8

The preparation of composite catalyst 8: A 500 ml water-free and oxygen-free flask with four necks is immersed in a thermostatic oil bath at the temperature of 80° C. 26.35 mmol of triethyl boron, $5.27 \times 10^{-2}$ mmol of TiCl$_4$, 65 ml of xylene, $5.27 \times 10^{-2}$ mmol of dimethyl sulfoxide, and $2.64 \times 10^{-2}$ mmol of the mixture (molar ratio 1:1) of methyl benzoate and ethyl p-hydroxybenzoate are added into the flask in order, nitrogen gas is introduced into the flask continuously, and the reaction is conducted at 80° C. for 20 min. The composite catalyst 8 is obtained.

The trimerization process: After 100 ml of CDT is added to the flask, butadiene is introduced to the flask such that the pressure in the flask is maintained at 0.3 MPa, and the reaction is conducted at the temperature of 80° C. for 60 min. After that, $5.27 \times 10^{-2}$ mmol of water is added to terminate the reaction. The reaction liquid is weighed and then filtered, and the resulting filtrate is determined by gas chromatography.

As a result, the composite catalyst 8 has the activity of 26635.8 g CDT/g $_{Ti}$/h and CDT selectivity of 96.73%.

Example 9

The preparation of composite catalyst 9: The preparation of the composite catalyst 8 in example 8 is repeated using 69 ml of n-hexane in place of 68 ml of xylene.

The trimerization process: According to the trimerization process of example 8.

As a result, the composite catalyst 9 has the activity of 25432.7 g CDT/g $_{Ti}$/h and CDT selectivity of 98.29%.

Example 10

The preparation of composite catalyst 10: A 500 ml water-free and oxygen-free flask with four necks is immersed in a thermostatic oil bath at the temperature of 40° C. 55 ml of toluene, 2.64 mmol of aluminium diethyl monochloride, 1.32 ml of thionyl chloride, $5.27 \times 10^{-2}$ mmol of TiCl$_4$, and 0.105 mmol of methyl benzoate are added into the flask in order, nitrogen gas is introduced into the flask continuously, and the reaction is conducted at 40° C. for 300 min. The composite catalyst 10 is obtained.

The trimerization process: After 192 ml of CDT is added to the flask, butadiene is introduced to the flask such that the pressure in the flask is maintained at 0.7 MPa, the temperature is raised to 70° C., and the reaction is conducted for 120 min. After that, 0.132 mmol of water is added to terminate the reaction. The reaction liquid is weighed and then filtered, and the resulting filtrate is determined by gas chromatography.

As a result, the composite catalyst 10 has the activity of 20241.0 g CDT/g $_{Ti}$/h and CDT selectivity of 98.65%.

Example 11

The preparation of composite catalyst 11: A 500 ml water-free and oxygen-free flask with four necks is immersed in a thermostatic oil bath at the temperature of 40° C. 110 ml of toluene, 0.88 mmol of aluminium diethyl monochloride, 1.32 ml of thionyl chloride, $5.27 \times 10^{-2}$ mmol of TiCl$_4$, and 0.105 mmol of methyl benzoate are added into the flask in order, nitrogen gas is introduced into the flask continuously, and the reaction is conducted at 40° C. for 300 min. The composite catalyst 11 is obtained.

The trimerization process: According to the trimerization process of example 10.

As a result, the composite catalyst 11 has the activity of 22762.5 g CDT/g $_{Ti}$/h and CDT selectivity of 96.37%.

Example 12

The preparation of composite catalyst 12: A 500 ml water-free and oxygen-free flask with four necks is immersed in a thermostatic oil bath at the temperature of 40° C. 110 ml of toluene, $5.27 \times 10^{-2}$ mmol of methyl benzoate, 2.64 mmol of aluminium diethyl monochloride, 1.32 ml of thionyl chloride, and $5.27 \times 10^{-2}$ mmol of TiCl$_4$ are added into the flask in order, nitrogen gas is introduced into the flask continuously, and the reaction is conducted at 40° C. for 300 min. The composite catalyst 12 is obtained.

As a result, the composite catalyst 12 has the activity of 25535.1 g CDT/g $_{Ti}$/h and CDT selectivity of 96.41%.

Example 13

The preparation of composite catalyst 13: A 500 ml water-free and oxygen-free flask with four necks is immersed in a thermostatic oil bath at the temperature of 40° C. 110 ml of toluene, 5.27 mmol of aluminium ethyl dichloride, 0.105 mmol of dimethyl sulfoxide, $5.27 \times 10^{-2}$ mmol of TiCl$_4$, and 1.32 mmol of ethyl formate are added into the flask in order, nitrogen gas is introduced into the flask continuously, and the reaction is conducted at 40° C. for 15 min. The composite catalyst 13 is obtained.

The trimerization process: After 58 ml of toluene is added to the flask, butadiene is introduced such that the pressure in the flask is maintained at 0.1 MPa, the temperature is raised to 70° C., and the reaction is conducted for 60 min. After that, $5.27 \times 10^{-2}$ mmol of ethanol is added to terminate the reaction. The reaction liquid is weighed and then filtered, and the resulting filtrate is determined by gas chromatography.

As a result, the composite catalyst 13 has the activity of 20324.5 g CDT/g $_{Ti}$/h and CDT selectivity of 95.43%.

Comparative Example 1

The preparation of comparative catalyst 1: A 500 ml water-free and oxygen-free flask with four necks is immersed in a thermostatic oil bath at the temperature of 120° C. 1.05 mmol of sesquiethyl aluminum chloride, 380 ml of n-heptane, $5.27 \times 10^{-2}$ mmol of TiCl$_4$, and 1.32 mmol of the mixture (molar ratio 1:1) of thionyl chloride and dimethyl sulfoxide are added into the flask in order, nitrogen gas is introduced into the flask continuously, and the reaction is conducted at 120° C. for 600 min. The comparative catalyst 1 is obtained.

The trimerization process: Butadiene is introduced to the flask such that the pressure in the flask is maintained at 0.5 MPa, the temperature is raised to 180° C., and the reaction is conducted for 600 min. After that, $5.27 \times 10^{-2}$ mmol of water is added to terminate the reaction. The reaction liquid is weighed and then filtered, and the resulting filtrate is determined by gas chromatography.

As a result, the comparative catalyst 1 has the activity of 18002 g CDT/g $_{Ti}$/h and CDT selectivity of 92.81%.

Comparative Example 2

The preparation of comparative catalyst 2: A 500 ml water-free and oxygen-free flask with four necks is immersed in a thermostatic oil bath at the temperature of 80° C. 26.35 mmol of triethyl boron, $5.27 \times 10^{-2}$ mmol of TiCl$_4$, 68 ml of xylene, and $5.27 \times 10^{-2}$ mmol of dimethyl sulfoxide are added into the flask in order, nitrogen gas is introduced into the flask continuously, and the reaction is conducted at 80° C. for 20 min. The comparative catalyst 2 is obtained.

The trimerization process: After 100 ml of CDT is added to the flask, butadiene is introduced to the flask such that the pressure in the flask is maintained at 0.3 MPa, and the reaction is conducted at the temperature of 80° C. for 60 min. After that, $1.32 \times 10^{-2}$ mmol of n-butanol is added to terminate the reaction. The reaction liquid is weighed and then filtered, and the resulting filtrate is determined by gas chromatography.

As a result, the comparative catalyst 2 has the activity of 18101.2 g CDT/g $_{Ti}$/h and CDT selectivity of 93.6%.

Comparative Example 3

The preparation of comparative catalyst 3: A 500 ml water-free and oxygen-free flask with four necks is immersed in a thermostatic oil bath at the temperature of 40° C. 55 ml of toluene, 2.64 mmol of aluminium diethyl monochloride, 1.32 ml of thionyl chloride, and $5.27 \times 10^{-2}$ mmol of TiCl$_4$ are added into the flask in order, nitrogen gas is introduced into the flask continuously, and the reaction is conducted at 40° C. for 300 min. The comparative catalyst 3 is obtained.

The trimerization process: After 192 ml of CDT is added to the flask, butadiene is introduced to the flask such that the pressure in the flask is maintained at 0.7 MPa, the temperature is raised to 70° C., and the reaction is conducted for 120 min. After that, $5.27 \times 10^{-2}$ mmol of water is added to terminate the reaction. The reaction liquid is weighed and then filtered, and the resulting filtrate is determined by gas chromatography.

As a result, the comparative catalyst 3 has the activity of 18060.3 g CDT/g $_{Ti}$/h and CDT selectivity of 93.1%.

Comparative Example 4

The preparation of comparative catalyst 4: A 500 ml water-free and oxygen-free flask with four necks is immersed in a thermostatic oil bath at the temperature of 20° C. 165 ml of toluene, $5.27 \times 10^{-2}$ mmol of TiCl$_4$, 1.32 mmol of dimethyl sulfoxide, and 52.7 mmol of n-butyl lithium are added into the flask in order, nitrogen gas is introduced into the flask continuously, and the reaction is conducted at 20° C. for 300 min. The comparative catalyst 4 is obtained.

The trimerization process: After 165 ml of toluene is added to the flask, butadiene is introduced such that the pressure in the flask is maintained at 1 MPa, the temperature is raised to 80° C., and the reaction is conducted for 15 min. After that, $5.27 \times 10^{-2}$ mmol of water is added to terminate the reaction. The reaction liquid is weighed and then filtered, and the resulting filtrate is determined by gas chromatography.

As a result, the comparative catalyst 4 has the activity of 18156.5 g CDT/g $_{Ti}$/h and CDT selectivity of 93.8%.

As seen from comparison of the invention examples and comparative examples, when used for the trimerization of butadiene to CDT, the catalysts of the present invention exhibit a higher catalytic activity and CDT selectivity than those of the comparative examples.

What is claimed is:

1. A composite catalyst trimerization of butadiene to 1,5,9-cyclododecatriene consisting of
   (A) a titanium compound catalyst active component, wherein the titanium compound is one or more selected from TiCl$_4$, TiCl$_2$R$_{4-z}$ or TiCl$_z$(OR)$_{4-z}$, wherein Z=1, 2 or 3, OR is alkoxy, R is alkyl having 1-20 carbons,
   (B) an organometallic compound co-catalyst component selected from one or more of methyl lithium, n-butyl lithium, n-hexyl lithium, sec-butyl lithium,
   (C) a sulfoxide compound catalyst-modifying component selected from one or more of dimethyl sulfoxide, thionyl chloride, diphenyl sulfoxide, and trimethylsulfoxonium iodide,
   (D) a monoester compound catalyst-modifying component selected from one or more of the group consisting of methyl p-hydroxybenzoate, ethyl p-hydroxybenzoate, butyl p-hydroxybenzoate, methyl aminobenzoate, ethyl aminobenzoate, butyl aminobenzoate, methyl p-benzenesulfonate, ethyl p-benzenesulfonate, butyl p-benzenesulfonate, methyl salicylate, ethyl salicylate and butyl salicylate, and
   (E) a solvent component selected from one or more of propane, n-butane, isobutane, n-pentane, isopentane, neopentane, n-hexane, cyclohexane, n-heptane, n-octane, benzene, toluene, xylene, 1,5,9-cyclododecatriene.

2. The composite catalyst according to claim 1, wherein: the molar ratio of the organometallic compound co-catalyst component (B) to the titanium compound catalyst active component (A) is 1-1000:1;
   the molar ratio of the sulfoxide compound catalyst-modifying component (C) to the titanium compound catalyst active component (A) is 1-30:1;
   the molar ratio of the monoester compound catalyst-modifying component (D) to the titanium compound catalyst active component (A) is 0.1-50:1;
   the molar ratio of the solvent component (E) to the titanium compound catalyst active component (A) is 5000-30000:1.

3. The composite catalyst according to claim 2, wherein: the molar ratio of the organometallic compound co-catalyst component (B) to the titanium compound catalyst active component (A) is 20-500:1; and
   the molar ratio of the monoester compound catalyst-modifying component (D) to the titanium compound catalyst active component (A) is 1-30:1.

4. The composite catalyst according to claim 1, wherein the titanium compound catalyst active component (A) comprises one or more of titanium tetrachloride, titanium tetraethoxide, and triethoxytitanium chloride.

5. A process for preparing the composite catalyst according to claim 1, wherein said process comprises:
   adjusting a temperature of an oxygen-free and water-free reaction system for preparing the composite catalyst to a preparation temperature of the catalyst, and
   adding to the reaction system the titanium compound catalyst active component (A), the organometallic compound co-catalyst component (B), the sulfoxide compound catalyst-modifying component (C), the monoester compound catalyst-modifying component (D), and the solvent component (E) in a specified proportion under stirring,
   wherein a time needed for preparing the composite catalyst is 15-600 minutes, timing from an end of addition of all the components,
   a temperature of preparing the composite catalyst is 20-120° C., and nitrogen or helium or argon is continuously introduced during the preparation.

6. The process for preparing the composite catalyst according to claim 5, wherein:
   the time needed for preparing the composite catalyst is 20-300 minutes, timing from the end of addition of all the components; and
   the temperature of preparing the composite catalyst is 25-80° C.

7. A catalyzation process comprising adding the composite catalyst according to claim 1 to a butadiene to 1,5,9-cyclododecatriene trimerization reaction system, introducing butadiene to the trimerization reaction system and catalyzing the trimerization of butadiene to 1,5,9-cyclododecatriene.

8. The process of claim 7, comprising:

adding the composite catalyst and a solvent for trimerization to the trimerization reaction system, wherein the molar ratio of the solvent for trimerization to the titanium compound catalyst active component (A) is 10000-50000:1;

introducing the butadiene continuously to start the reaction, wherein the temperature for the trimerization is 20-200'C; the pressure for the trimerization is 0.1-1 MPa; and time for the trimerization is 10-600 minutes; and adding the termination agent to terminate the reaction, wherein a molar ratio of the termination agent to the titanium compound catalyst active component (A) of the composite catalyst is 0.1-5:1, the solvent for trimerization comprises one or more selected from the group consisting of propane, n-butane, isobutane, n-pentane, isopentane, neopentane, n-hexane, cyclohexane, n heptane, n-octane, benzene, toluene, xylene, and 1,5,9-cyclododecatriene, the termination agent comprises water, monohydroxy alcohol, or the mixture of water and monohydroxy alcohol in any proportion, wherein the monohydroxy alcohol is one or more selected from the group consisting of methanol, ethanol and n-butanol.

9. The process of claim 8, wherein:

the molar ratio of the solvent for trimerization to the titanium compound catalyst active component (A) is 18000-30000:1;

the temperature for the trimerization is 25-120° C.; the pressure for the trimerization is 0.2-0.7 MPa; and the time for the trimerization is 15-300 minutes; and the solvent for trimerization comprises one or more selected from the group consisting of propane, n-butane, isobutane, n-pentane, isopentane, neopentane, n-hexane, cyclohexane, n-heptane, n-octane, benzene, toluene, xylene, 1,5,9-cyclododecatriene.

* * * * *